United States Patent
Schwartz

(10) Patent No.: US 6,383,817 B2
(45) Date of Patent: May 7, 2002

(54) CADMIUM IS A RISK FACTOR FOR HUMAN PANCREATIC CANCER

(75) Inventor: Gary G. Schwartz, Winston-Salem, NC (US)

(73) Assignee: Wake Forest University, Winston-Salem, NC (US)

( * ) Notice: Subject to any disclaimer, the term of this patent is extended or adjusted under 35 U.S.C. 154(b) by 0 days.

(21) Appl. No.: 09/747,468

(22) Filed: Dec. 22, 2000

Related U.S. Application Data

(60) Provisional application No. 60/173,760, filed on Dec. 30, 1999.

(51) Int. Cl.$^7$ ................................................. G01N 33/20
(52) U.S. Cl. ............................ 436/81; 436/63; 436/64; 436/73; 436/74
(58) Field of Search ............................. 436/63, 64, 73, 436/74, 81, 171, 813

(56) References Cited

U.S. PATENT DOCUMENTS 4,734,283 A    3/1988    Sirén

OTHER PUBLICATIONS

Sorahan et al. *Occupational & Enviromental Medicine*, vol. 52, pp. 804–812, 1995.*

Börjesson et al. *Occupational & Environmental Medicine*, vol. 54, pp. 424–431, 1997.*

Järup et al. *Occupational & Environmental Medicine*, vol. 55, pp. 755–759, 1998.*

Waalkes et al. *Critical Reviews in Toxicology*, vol. 22(3,4), pp. 175–201, 1992.*

Schrauzer et al. *Bioinorganic Chemistry*, vol. 7(1) pp. 35–56, 1977.*

Ojajärvi, I. Anneli, et al., Occupational exposures and pancreatic cancer: a meta–analysis, *Occup. Environ. Med.,* vol. 57, pp. 316–324 (2000).

Schwartz, Gary G., et al., Is Cadmium a Cause of Human Pancreatic Cancer, *Cancer Epidemilogy, Biomarkers & Prevention,* vol. 9, pp. 139–145 (Feb. 2000).

International Search Report, International Application No. PCT/US00/34926 dated Apr. 4, 2001.

* cited by examiner

*Primary Examiner*—Maureen M. Wallenhorst
(74) *Attorney, Agent, or Firm*—Myer Bigel Sibley & Sajovec

(57) ABSTRACT

The present invention provides a method of screening for risk of pancreatic cancer in a subject, wherein the presence or absence of increased levels of cadmium in the subject is detected and wherein the presence of increased levels of cadmium in the subject indicates that the subject is at increased risk of pancreatic cancer.

16 Claims, No Drawings

CADMIUM IS A RISK FACTOR FOR HUMAN PANCREATIC CANCER

RELATED APPLICATIONS

This application claims the benefit of Provisional Application Ser. No. 60/173,760, filed Dec. 30, 1999, the disclosure of which is incorporated by reference herein in its entirety.

FIELD OF THE INVENTION

The present invention concerns methods of screening for risk of, or predisposition to, pancreatic cancer.

BACKGROUND OF THE INVENTION

Cancer of the pancreas is an important cause of cancer mortality in developed countries and accounts for more than 28,000 deaths in the U.S. per year. Pancreatic cancer produces few specific symptoms in its early stages and usually is detected at an advanced and incurable stage. This contributes to pancreatic cancer having the worst survival of any major cancer; the average survival after diagnosis is less than 6 months and fewer than 5% of patients survive 5 years (Rosenberg, L. (1997) *Pancreatol.* 22:81–93; Flanders and Foulkes (1996) *J. Med. Genet.* 33:889–898).

The etiology of pancreatic cancer is obscure (see refs Anderson, et al. (1996) In D. Schottenfeld, J. F. Fraumeni, J. F., Jr. Cancer Epidemiology and Prevention, 2$^{nd}$ Ed., Oxford University Press, New York, pp. 725–771; Fontham and Correa (1989) *Surg. Clin. North Am.* 69:551–567; Fryzek, et al. (1997) *GI Cancer* 2:99–100 for reviews of the epidemiology). Incidence rates for pancreatic cancer increase exponentially with age beginning at about age 40, are approximately 50% higher among males than females, and are higher among blacks than whites. Despite considerable epidemiologic study, the only modifiable risk factor that has been established is cigarette smoking. However, the identity of the carcinogen(s) in cigarette smoke is unknown. Few strong occupational risks have been detected, although moderate risks have been associated with several industries, including metal working occupations and pesticide exposure (Pietri and Clavel (1991) *Br. J. Ind. Med.* 48:583–587). Mapping of U.S. mortality rates from pancreatic cancer has identified significantly elevated rates in southern Louisiana (Blot, et al. (1978) *Cancer* 42:373–380), but the cause of that cluster remains largely unexplained.

Toxicological properties of cadmium. Cadmium, atomic number 48, is a soft, silver-white metal that is found naturally at low levels in rocks and soil. Cadmium is used in a variety of industries, e.g., in nickel-cadmium batteries, electroplating, as a component in metallurgical and brazing-soldering alloys, in pigments, and as a stabilizer for plastic. Most of the cadmium produced in the U.S. is extracted during the smelting of other metals, such as zinc, lead, or copper. Smelters are a major source of airborne cadmium contamination. Other sources of environmental cadmium are the burning of fossil fuels and waste materials, and the use of phosphate fertilizers and sewage sludge (I.A.R.C. IARC Monographs on the evaluation of carcinogenic risks to humans. Vol. 58. Beryllium, cadmium, mercury and exposures in the glass manufacturing industry. IARC, Lyon, France; Yost, K. J. (1979) *Hlth. Persp.* 28:5–16; Cabrera, et al. (1998) *Rev.Environ. Contam. Toxicol.* 154:55–81; Davis, R. D. Cadmium in sludges used as fertilizer. Experientia Suppl., 50:55–65, 1986).

Cadmium that is present in soil as the result of industrial emissions or fertilization can be taken up selectively by edible plants, producing cadmium concentrations many times that of the surrounding soil (Korzun and Heck (1990) *J. Air Waste Manage. Assoc.* 40:1220–1226). Similarly, many water plants biomagnify the levels of cadmium in the surrounding water. Cadmium levels in fish, especially Mollusca and Crustacea (e.g., oysters, shrimp, crab and crayfish), can be greatly elevated (Noqvi, et al. (1993) *J. Environ. Sci. Hlth. B* 28:473–485). Most of the cadmium in crustaceans is contained within a single organ, the hepatopancreas (Jorhem, et al. (1994) *Arch. Environ. Contam. Toxicol.* 26:137–142; White and Rainbow (1986) *Com. Biochem. Physiol. C* 13:111–116; Engel, D. W. (1983) *Science Total Environ.* 28:129–140), which is commonly consumed by humans. For example, plants grown for 7 days in 0.00224 parts per billion (ppb) cadmium were fed to Louisiana red swamp crayfish (*Procambarus clarkii*) for 14 days. Accumulation of cadmium in hepatopancreata increased from 176.8 ppb on day 0 to 4,657.6 ppb on day 14 (Devi, et al. (1996) *Ecotoxicol. Environ. Safety* 33:38–43). Cadmium levels in edible crab (*Cancer pagurus*) may be as high as 30–50 parts per million (Overnell J. (1996) *Environ. Health Perspect.* 65:101–105). Consumption of one crab meal per week has been estimated to exceed the WHO provisionally tolerable cadmium intake of less than 500 $\mu$g (Lind, et al. (1995) *Food Chem.Toxicol.* 33:667–673; World Health Organization. Toxicological Evaluation of Certain Food Additives and Contaminants. WHO Food Additive Series 24, World Health Organization, Geneva, 1989).

Food is the main source of cadmium for the non-smoking population. Estimates of dietary cadmium intake worldwide range from 10 to 40 $\mu$g/day in nonpolluted areas to several hundreds of micrograms in cadmium-polluted regions. In the U.S., the average person consumes approximately 30 $\mu$g cadmium per day in food and absorbs 1–3 $\mu$g from the gastrointestinal tract. Smoking is an important source of cadmium exposure (Jarop, et al. (1998) *Scand. J. Work Environ. Health* 24: Suppl 1:1–51). One cigarette contains approximately 1–2 $\mu$g cadmium, and smokers absorb an additional 1–3 $\mu$g cadmium/day from the respiratory tract (Agency for Toxic Substances and Disease Registry. Toxicological profile for cadmium, April 1993 update. U.S. Publ. Hlth. Serv.).

Most of the cadmium in the body is bound to metallothioneins, low molecular weight proteins that function in the homeostasis of essential metals, e.g., zinc (Hamer, D. H. (1986) *Annu. Rev. Biochem.* 55:913–951; De Lisle, et al. (1996) *Am. J. Physiol.* 271:C2204–1110). The cadmium-metallothionein complex is distributed to various tissues and organs and ultimately is reabsorbed in kidney tubuli Ohta and Cherian (1991) *Toxicol. Appl. Pharmacol.* 107:63–72). Because the body has no mechanism for the excretion of cadmium, cadmium accumulates in tissues. The half-life of cadmium in kidney cortex is 10–30 years. In humans, the largest amount of cadmium is deposited in the kidneys and liver, followed by the pancreas and lungs.

In 1993, The International Agency for Research on Cancer (IARC) classified cadmium and cadmium compounds as known human carcinogens (i.e., category 1 compounds) (Boffetta, P. (1993) *Scand. J. Work Environ. Health* 19:67–70). The most convincing human data implicate cadmium as a carcinogen in the lung, with equivocal evidence at other sites (e.g., prostate (Potts, C. L. (1965) *Ann. Occup. Hyg.* 8:55–61) and kidney (Kolonel, L. N. (1976) *Cancer* 37:1782–1787)).

SUMMARY OF THE INVENTION

The present invention is based on the recognition that elevated body levels of cadmium in a subject is a risk factor for pancreatic cancer. Greater levels of cadmium in the body indicate greater susceptibility to pancreatic cancer.

To our knowledge, this is the first report to propose that cadmium is a cause of human pancreatic cancer.

Accordingly, the present invention provides a method of screening for risk of pancreatic cancer in a subject, comprising detecting the presence or absence of increased levels of cadmium in the subject, with the presence of increased levels of cadmium in the subject indicating the subject is at increased risk of pancreatic cancer.

The present invention is explained in greater detail in the specification set forth below.

DETAILED DESCRIPTION OF THE INVENTION

The present invention is primarily intended for human subjects, but may be carried out on animal subjects, particularly mammalian subjects such as cows, horses, pigs, sheep, goats, dogs, rats, mice, rabbits and the like for veterinary medicine purposes or drug screening and control purposes.

The present invention can be carried out with any human subject, including adult, adolescent and juvenile subjects; male and female subjects, and subjects of any race.

By screening for increased risk herein is meant detecting an increased risk of susceptibility or increased susceptibility to pancreatic cancer. Thus the present invention is intended primarily for prognostic purposes, although the invention may also be used for diagnostic purposes to confirm a suspected diagnosis of pancreatic cancer.

As noted above, the present invention provides a method of screening for risk of pancreatic cancer in a subject, comprising detecting the presence or absence of increased levels of cadmium in the subject, with the presence of increased levels of cadmium in the subject indicating the subject is at increased risk of pancreatic cancer. Where increased levels of cadmium are detected, those increased levels and/or the increased risk the step of providing a report of said increased risk of pancreatic cancer (i.e., to the subject, or in the case of a non-human subject such as a farm animal to the owner of the subject). The present invention is particularly useful in encouraging early intervention with the subject. Thus, if increased levels of cadmium are detected and increased risk is detected, any of a variety of interventions may be prescribed. These include:

(a) prescribing a dietary, occupational, or lifestyle change to decrease the intake of cadmium by said subject, and/or decrease other risk factors for pancreatic cancer (e.g., avoiding occupational exposure to cadmium, avoiding smoking, avoiding food sources containing greater quantities of cadmium, etc.;

(b) prescribing an increased monitoring of said subject for pancreatic cancer (which may be carried out in accordance with known techniques), or (c) both (a) and (b) above.

The step of detecting cadmium levels may be carried out by any suitable technique. Numerous such techniques are known. Cadmium may be detected in a urine or serum sample collected from the subject, or may be detected in a tissue sample such as blood, hair, liver, kidney, or pancreas collected from the subject. By "increased levels" of cadmium in the subject is meant an increase in cadmium above, or substantially above, the average cadmium concentration in the general population for the given tissue or sample collected.

The present invention is explained in greater detail in the Examples set forth below.

EXAMPLE 1

Cadmium is a Cause of Human Pancreatic Cancer
Pancreatic Cancer Risk Factors

Many of the known risk factors for pancreatic cancer are intelligible in terms of increased exposure to cadmium (see Table 1). For example, the increasing incidence rate of pancreatic cancer with age is intelligible because cadmium levels are undetectable in the pancreata of newborns and accumulate with age, reaching their peak at about age 50 (Vuori, et al. (1979) *Scand. J. Work Environ. Health.* 5:16–22).

The increased risk associated with smoking also is understandable and is consistent with the cadmium content of cigarettes. The mean cadmium content in the fat of smokers is 4 times that of nonsmokers (Mussalo-Rauhamaa, et al. (1986) *Arch. Environ. Health* 41:49–55). Autopsy studies demonstrate consistently that the pancreata of smokers contain approximately twice the amount of cadmium as the pancreata of age-matched nonsmokers (Elinder, et al. (1976) *Arch. Environ. Health* 31:292–302; Kowal, et al. (1979) *J. Toxicol. Environ. Health* 5:995–1014).

The significantly elevated rates for pancreatic cancer in Louisiana also are intelligible. Industrial activity in Louisiana has contaminated much of the wetlands with cadmium (Tchounwou, et al. (1996) *Rev. Environ. Health* 11:191–203). For example, sampling of indoor and outdoor air in 53 households in Louisiana revealed that 64 of 315 samples (20.3%) exceeded the Environmental Protection Agency's guidelines for cadmium (Lemus, et al. (1996) *Rev. Environ. Health* 11:179–189). South Louisiana is home to the Arcadian (Cajun) population and is one of the largest rice-producing regions in the U.S. A case-control study of pancreatic cancer in Louisiana found significantly increased risk for rice consumption among Cajuns, with evidence of a dose-response (Falk, et al. (1988) *Am. J. Epidemiol.* 128:324–336). Rice grown in cadmium-polluted regions is known to contain high levels of cadmium (Ikeda, M. (1992) *IARC Sci. Publ.* 118:65–72). The case-control study also found a significantly increased risk for seafood consumption, at least among women. As noted above, extremely high levels of cadmium have been detected in Louisiana seafood (Modigosky, et al. (1991) *Arch. Environ. Contam. Toxicol.* 20:253–258). Significantly increased risks for fish consumption also were found in a case-control study of pancreatic cancer in The Netherlands (Bueno de Mesquita, et al. (1991) *Int. J. Cancer* 48:540–549), many areas of which (e.g., the river Meuse and the Kempen) are heavily contaminated with cadmium (Albering, et al. (1999) *Environ. Health Perspect.* 107:37–43; Copius Peereboom-Stegeman and Copius Peereboom (1989) *Ecotoxicol. Environ. Safety* 18:93–108).

Finally, large risks for pancreatic cancer have not been detected in occupational studies (Mack, et al. (1985) *Am. J. Ind. Med.* 7:253–266; Falk, et al. (1990) *Am. J. Ind. Med.* 18:565–576), however, numerous studies demonstrate significantly increased risks for workers exposed to pesticides (Alavanja, et al. (1990) *J. Natl. Cancer Inst.* 16:840–848; Partanen, et al. (1994) *Am. J. Ind. Med.* 25:851–866; Forastiere, et al. (1993) *Scand. J. Work Environ. Health* 19:382–389; Cantor and Silberman (1999) *Am. J. Ind. Med.* 36:239–247) and for workers manufacturing paints and pigments (Raymond and Bouchardy (1990) *Bull. Cancer* 77:47–68; Norell et al. (1986) *Br. J. Ind. Med.* 43:775–778; Sheffet, et al. (1982) *Arch. Environ. Health*

37:44–52). Increased risks also have been observed repeatedly for individuals employed in metalworking occupations (Maruchi, et al. (1979) *Mayo Clinic Proc.* 54:245–249; Mallin, et al. (1986) *Am. J. Ind. Med.* 10:127–141; Rotimi, et al. (1993) *Am. J. Ind. Med.* 24:485–498; Park and Mirer (1996) *Am. J. Ind. Med.* 30:664–673; Silverstein, et al. (1988) *J. Occup. Med.* 30:706–714; Sparks and Wegman (1980) *J. Occup. Med.* 22:733–736). Exposure to cadmium is common to these occupations. For example, cadmium is a significant contaminant of both pesticides and pigments. Similarly, many metal workers are exposed to cadmium and cadmium fuime, e.g., via welding or soldering (Beton, et al. (1966) *Brit. J. Industr. Med.* 23:292–301; Weiss and Lesser (1997) *South. Med. J.* 90:665–671). Solderers are known to have significantly elevated levels of cadmium in serum (Smith, et al. (1986) *Br. J. Ind. Med.* 43:663–666) and to have a significantly increased risk of pancreatic cancer (Ji, et al. (1999) *China. Am. J. Ind. Med.* 35:76–81). These risk factors are summarized in Table 1.

TABLE 1

Cadmium Risk Factors.

| Risk Factor | Explanation |
| --- | --- |
| Age | Cadmium accumulates in the pancreas with age. |
| Smoking | Cadmium is a constituent of cigarettes. The pancreata of smokers contains twice the cadmium of non-smokers |
| Geography | Increased rates in Louisiana are consistent with cadmium pollution. International mortality rates are positively correlated with dietary cadmium. |
| Occupation | Occupations with high exposure to cadmium show increased mortality from pancreatic cancer. |

Experimental Determination of Cadmium's Role in Pancreatic Cancer

In 1977, Schrauzer et al. ((1977) *Bioinorganic Chem.* 7:35–56) correlated data on dietary consumption of various trace elements per capita in 29 countries with the corresponding age-adjusted mortality rates from various cancers. Their goal was to investigate the confounding influence of trace elements (e.g. cadmium) on the anti-cancer properties of selenium. They noted a significant, positive correlation between the estimated dietary intake of cadmium and pancreatic cancer mortality in both men and women (r=0.48 and 0.25, for men and women, respectively). Thus, their ecologic study provides tentative support that exposure to cadmium increases the risk of pancreatic cancer. However, the question of greatest interest, i.e., whether individuals with high exposure are at increased risk, cannot be answered by ecologic data but rather by direct analysis of individuals exposed to cadmium.

Toward this goal, the MEDLINE database was searched for the period from January 1966 through March 1999, in all languages, for reports of the mortality of cadmium exposed workers. Papers cited in these reports also were reviewed. Twenty-five papers were obtained. The majority of these papers concerned the association between cadmium and cancers of the lung and/or prostate. None of the studies were designed to investigate the association of cadmium exposure and cancer of the pancreas. However, five of these studies provided numerical data on observed and expected deaths from pancreatic cancer. Because the number of pancreatic cancer deaths in each of the studies was small, the data was combined in a meta-analysis in order to obtain a more precise estimate of the risk associated with cadmium exposure. The meta-analysis was restricted to the most recent report on each cohort. After removing duplicate data (updates on cohorts that were reported previously), data were available for four cohorts (Elinder, et al. (1985) *Br. J. Ind. Med.* 42:651–5; Sorahan, et al. (1995) *Occup. Environ. Med.* 52:804–12; Järup, et al. (1998) *Occup. Environ. Med.* 55:755–9). A summary SMR (×100) and 95% confidence interval (95%CI) for pancreatic cancer after testing for homogeneity of the study-specific SMRs were estimated. The summary estimate was computed under a fixed effects model (Frumkin and Berlin (1988), *Amer. J. Ind. Med* 14: 79–95; Petitti, D. B. (1994) Meta-Analysis Decision Analysis and Cost-Effectiveness Analysis: Methods for Quantitative Synthesis in Medicine. Oxford University Press, pp. 115-130).

All the studies involved cohorts of males; Järup et al. also reported data for females ((1998) *Occup. Environ. Med.* 55:755–9). To determine whether the data on females affected the summary SMR, two meta-analyses, one comprised of male workers, and another comprised of male workers with data on females included as a separate cohort were performed.

Table 2 presents characteristics of the available studies. There is no evidence of heterogeneity of the study-specific SMRs for males (p=0.762). The estimated summary SMR for males is 162 (94–279), p=0.082 for the test of a significant difference from SMR=100. The SMR of 220 for females did not differ significantly from the summary SMR for males (162) (p=0.766). The test of heterogeneity for the SMRs for the four study cohorts (men and women) also is not significant (p=0.889). Therefore a summary estimate was calculated combining the data from males and females. The overall summary SMR is 166 (98–280), p=0.059.

TABLE 2

Characteristics of Available Studies.

| Study | Population | Cohort Size | Follow-up Period | Deaths Obs | Deaths Exp | SMR | 95% CI |
| --- | --- | --- | --- | --- | --- | --- | --- |
| Elinder, et al. (1985) | Male cadmium-nickel battery workers; Oskarshamn, Sweden | 522 | 1951–89 | 3 | 2.3 | 130 | 27–380 |
| Sorahan, et al. (1995) | Male copper cadmium alloy workers; England and Wales | 347 | 1946–92 | 4 | 1.8 | 218 | 59–558 |

TABLE 2-continued

Characteristics of Available Studies.

| | | | | | | | |
|---|---|---|---|---|---|---|---|
| Järup et al. (1998) | Battery workers; Kalmar, Sweden | | | | | | |
| | Males | 717 | 1951–92 | 6 | 4.0 | 148 | 55–323 |
| | Females | 187 | 1951–92 | 1 | 0.4 | 220 | 6–1226 |

| Meta-analysis | Test of Homogeneity of the SMRs | Summary SMR and 95% CI | | Test of Summary SMR = 100 |
|---|---|---|---|---|
| 1, 2, 3 (males only) | p = 0.762 | 162 | 94–279 | p = 0.082 |
| 1, 2, 3 | p = 0.889 | 166 | 98–280 | p = 0.059 |

The data summarized in Table 2, illustrate the gain in precision obtained from the meta-analysis. Although the total number of deaths is modest, the consistency of the data in the four cohorts, the elevated risks in males and females, and the findings of the meta-analyses demonstrate that exposure to cadmium increases the risk of death from pancreatic cancer.

It is possible that these results reflect the confounding effects of smoking. Although data on smoking histories generally were not available, the percentage of smokers among the Swedish cadmium workers was similar to that of the general Swedish population in the 1980's (Andersson, et al. (1984) *Toxicol. Environ. Chem.* 9:53–62). It is unlikely that the excess of pancreatic cancer among the British cadmium workers was the result of confounding by smoking since these workers did not experience an excess of lung cancer (18 cases observed vs. 17.84 expected). Conversely, because these cohorts experienced significantly increased mortality from competing causes (e.g., nephritis and nephrosis, and accidental poisoning by heavy metals and their fumes [ICD-8 E866]), the observed risk for pancreatic cancer may underestimate the true risk.

Biological Mechanism of Action of Cadmium

The meta-analysis suggests that individuals with increased exposure to cadmium have an increased risk of pancreatic cancer which may implicate cadmium as a carcinogen in the pancreas. In animals, both carcinogenic and anti-carcinogenic effects of cadmium have been described (Waalkes, et al. (1992) *Crit. Rev. Toxicol.* 22:175–201). However, the majority of evidence indicates that cadmium is indeed carcinogenic in the pancreas. Without wishing to be bound to any particular theory of the invention, possible mechanisms for cadmium's carcinogenicity include substitution of cadmium for zinc, transdifferentiation, and oncogene activation.

The substitution of cadmium for zinc may be a central mechanism underlying the carcinogenicity of cadmium. Zinc is an essential trace element that is required for the synthesis of DNA, RNA, and protein, and thus, for cell division (Prasad, A. S. (1983) *Clin. Gastroenterol.*, 12:713–741). The pancreas contains high levels of zinc. Conversely, there is no known human requirement for cadmium. Because cadmium and zinc lie in the same group of the periodic table and share many physical and chemical properties, cadmium can compete for zinc in biochemical reactions. One illustration of the importance of the zinc-cadmium relationship is that cadmium's effects on several biological systems, including the formation of tumors, can be suppressed by the simultaneous injection of zinc (Merali and Singhal (1976) *Br. J. Pharmacol.* 57:573–579; Waalkes, et al. (1980) *Cancer Res.* 49:4282–4288; Abshire, et al. (1996) *J. Toxicol. Environ. Health* 48:359–377; Warner, et al. (1984) *Teratology* 30:47–53).

Cadmium is one of the most potent agents known to induce transdifferentiation of the pancreas (Waalkes, et al. (1992) *Toxicol. Pathol.* 20:323–326). Transdifferentiation, or metaplasia, is a change from one differentiated cell type to another, e.g., from a mature pancreatic cell to a mature liver cell (hepatocyte) (Rao, et al. (1986) *Curr. Top. Dev. Biol.* 20:63–78; $^O$kada, T. S. (1986) *Dev.Growth Differ.* 28:213–221). Repeated injections of cadmium to rats induced hepatocytic foci in the pancreata of more than 93% of rats (Konishi, et al. (1990) *Toxicol Appl. Pharmacol.* 104:149–156). Because the process of metaplasia involves cellular dedifferentiation, proliferation, and ultimately redifferentiation (Yuan, et al. (1996) *Differentiation* 61:67–75), agents that induce metaplasia (i.e., cadmium) may place cells at increased risk for neoplasia (Parsa, et al. (1985) *Cancer Res.* 45:1285–1290; Preston-Martin, et al. (1990) *Cancer Res.* 50:7415–7421).

As noted above, cadmium is mitogenic to pancreatic cells (Kacew, et al. (1976) *Gen. Pharmacol.* 7:433–435). For example, relative to mice injected with saline, injection of mice with 4 mg/kg cadmium chloride caused a 2.5-fold increase in the incorporation of [$^3$H] thymidine in the pancreas. The increased DNA synthesis is thought to reflect the increased synthesis of metallothionein (Hellman, B. (1986) *Toxicology* 40:13–23; Andrews, et al. (1990) *Pancreas* 5:548–554). Injection of rats with 4 and 8 mg/kg cadmium caused a 9.8 and 17.9-fold increase in pancreatic metallothionein (Wormser and Calp (1988) *Experientia* 44:754–755). Cadmium is also carcinogenic in the pancreas. For example, injection of Wistar rats with cadmium chloride caused a significant increase in the incidence of pancreatic islet cell tumors (8.5 vs. 2.2%) (Poirier, et al. (1983) *Cancer Res.* 43:4575–4581). In addition to its direct effects on pancreatic cells, cadmium may influence carcinogenesis indirectly, e.g., by inducing specific genes such as metallothionein, or by acting as a toxin and thereby disrupting cellular function (Koropatnci and Zalups (1997) *Br. J. Pharmacol.* 120:797–806). For example, the cadmium-metallothionein can cause DNA strand breaks (Rossman, et al. (1992) *IARC Sci. Publ.* 118:367–375). Moreover, transgenic mice that overexpress metallothionein (metallothionein III) develop a selective and progressive degeneration of pancreatic acinar cells (Quaife, et al. (1998) *Toxicol. Appl. Pharmacol.* 148:148–157). It is intriguing in this regard that increased expression of metallothionein, as measured by immunohistochemistry, has been associated with metastasis, poor prognosis, and poor histologic grade in human pancreatic cancers (Ohshio, et al. (1996) *J. Cancer Res. Clin. Oncol.* 122:351–355).

Cadmium can induce or regulate the activation of several oncogenic proteins that are known to be overexpressed in human pancreatic cancers, e.g., ras proteins (Yamada- Okabe, et al. (1996) *J. Cell. Biochem.* 61:172–181; Voeller, et al. (1991) *Mol. Endocrin.* 5:209–216 ). In order for ras proteins to become oncogenic, a farnesyl group must be added. The enzyme normally responsible for this reaction, farnesyl:protein transferase, is a zinc metalloenzyme. Cadmium can substitute for zinc in this reaction and can farnesylate some H-ras motifs that are normally not affected by zinc (Zhang, et al. (1996) *Biochemistry* 35:8166–8171). Cadmium also induces expression of the c-fos oncogene (Wang and Templeton (1998) *J. Biol. Chem.* 273:73–79), which is increased in many pancreatic cancers (Soon Lee and Charalambous (1994) *Zentralbl. Pathol.* 140:271–275). Finally, cadmium can enhance the inititation of carcinogenesis induced by other carcinogens, such as dimethynitrosamine and hepatitis B, and inhibits DNA repair (Wade, et al. (1987) *Cancer Res.* 47:6606–6613; Sell and Illic (1994) *Carcinogenesis* 15:2057–2060; Beyersmann and Hechtenberg (1997) *Toxicol. Appl. Pharmacol.* 144:247–261; Nocentini, S. (1987) *Nucleic Acids Res.* 15:4211–4225).

In summary, cadmium can cause the transdifferentiation of pancreatic cells, increase the synthesis of pancreatic DNA, and regulate the expression of oncogenes that are implicated in pancreatic carcinogenesis. Thus, cadmium is a plausible pancreatic carcinogen.

EXAMPLE 2

Detection of Cadmium in Urine Specimens

Cadmium can be measured in blood, urine, and tissues by automic absorption spectrophotometry and can be measured in vivo by neutron activation analysis or x-ray fluorescence (Chettle, (1990) In Yasumura, S., Harrison, J. E., McNeil, K. G., Woodhead, A. D., Dilmanian, F. A., eds. Advances in in vivo body composition studies. New York: Plenum Press, pp. 247–257; Böjesson and Mattson (1995) *Appl. Radiat. Isot.* 46:571–576). The relative merits of sampling urine and blood for measuring exposure to cadmium have recently been discussed (Böjesson, et al. (1997) *Occup. Environ. Med.* 54:424–431; Järup, et al. (1997) *Scand. J. Work Environ. Health* 23:31–36). In general, blood cadmium reflects both cumulative body burden and recent exposure. Urinary cadmium reflects the cumulative body burden of cadmium long after exposures have ceased, but may be inaccurate if renal tubular damage has occurred.

Urine is a well-studied dosimeter of lifetime exposure to cadmium. A spot collection of urine, corrected for creatinine, has been found to be as reliable as a 24-hour collection.

After the urine specimen is obtained from a human subject, a portion of the specimen is taken for the measurement of creatinine, as explained below, so that the metal contents can be expressed per mg/creatinine. At least 5 ml is frozen at −40° C. until delivery to the laboratory for analysis. Less that 10 cc total urine is needed from each participant to complete the analyses.

Cadmium, zinc, and copper levels in the sample are determined through graphite furnace atomic absorption spectrophotometry in accordance with known techniques. Atomic absorption spectrophotometry is a well established, highly sensitive and specific method for detecting metals.

In addition to the measurements of cadmium in urine, urine samples are also analyzed for creatinine, in order to generate a measurement of cadmium excretion per gram creatinine. The purpose of the creatinine correction is to adjust the metal measurement for the diluteness of the urine sample. The creatinine measurements are made using the bitric acid method in accordance with known techniques.

Retinol-binding protein (RBP) is a measure of low molecular weight proteinurea known to be increased by kidney damage and by exposure to cadmium in particular. Increased RBP in urine is a well studied measure of the effects of cadmium on the kidney and thus can serve as a good surrogate marker for the effect of cadmium damage on the pancreas. RBP measurements are performed by radio-immunoassay in accordance with known techniques.

Urine is stored in plastic, heavy-metal free containers (purchased from Corning Glass Works).

Data from urine tests is given in Table 3 below, Basically, the data shows 17 samples from patients with pancreatic cancer that were tested via two methods: Inductively-coupled plasma mass spectrophotometry (ICP) and graphite furnace atmoic absorption spectrophotometry (GFAAS). Below this are data from a pool of 300 "normal" individuals who have been tested. As will be seen see, very few of the "normal" individuals test higher than 2.0 ng/ml, whereas approximately 6 out of 17 pancreatic patients had much higher levels of cadmium.

TABLE 3

Cadmium in Urine Samples of Pancreatic Cancer Patients.

| Sample | ICP ng/mL | GFAAS ng/mL | Average ng/mL |
|---|---|---|---|
| 7 | ND | ND | ND |
| 3 | 0.3 | ND | 0.3 |
| 5B | 0.4 | ND | 0.4 |
| 12 | ND | 0.4 | 0.4 |
| 18 | 0.5 | 17* | 0.5 |
| 17 | ND | 0.8 | 0.8 |
| 14 | 0.4 | 1.4 | 0.9 |
| 8 | 28.5* | 1.1 | 1.1 |
| 13 | 1.3 | 12* | 1.3 |
| 16 | 11.5* | 1.4 | 1.4 |
| 9 | 1.5 | 24* | 1.5 |
| 11 | 2.4 | 1.7 | 2.1 |
| Z | 3.3 | 2.7 | 3.0 |
| 2 | 2.8 | 4.4 | 3.6 |
| 10 | 5.9 | 2.5 | 4.2 |
| 6 | 3.3 | 5.7 | 4.5 |
| 15 | 13.5* | 4.6 | 4.6 |

Distribution of typical results for 300 "normal" samples in ng/mL

| | |
|---|---|
| 0.5 | 53.0% |
| 0.5–1.0 | 26.7% |
| 1.0–1.5 | 10.3% |
| 1.5–2 | 5.7% |
| 2.05 | 4.0% |
| >5 | 0.3% |

*Outliers, data not included.

The foregoing is illustrative of the present invention, and is not to be construed as limiting thereof. The invention is defined by the following claims, with equivalents of the claims to be included therein.

What which is claimed is:

1. A method of screening for risk of pancreatic cancer in a subject, comprising:
   detecting the presence or absence of increased levels of cadmium in said subject as compared to a control population;
   the presence of increased levels of cadmium in said subject indicating the subject is at increased risk of pancreatic cancer.

2. A method according to claim 1, wherein said detecting step is followed by the step of providing a report of said increased risk of pancreatic cancer.

3. A method according to claim 1, wherein said detecting step is followed, upon detection of increased levels of cadmium in said subject, by the steps of:

(a) prescribing a dietary, occupational, or lifestyle change to decrease the intake of cadmium by said subject;

(b) prescribing an increased monitoring of said subject for pancreatic cancer, or (c) both (a) and (b) above.

4. A method according to claim 1, wherein said detecting step is carried out by detecting increased cadmium levels in a biological fluid collected from said subject.

5. A method according to claim 1, wherein said detecting step is carried out by detecting increased cadmium levels in a urine sample collected from said subject.

6. A method according to claim 1, wherein said detecting step is carried out by detecting increased cadmium levels in a tissue sample collected from said subject.

7. A method according to claim 6, wherein said tissue sample is selected from he group consisting of blood, hair, liver, kidney, and pancreas.

8. The method according to claim 6, wherein said tissue sample is blood.

9. A method according to claim 6, wherein said tissue sample comprises a blood serum sample.

10. A method of screening for increased predisposition to pancreatic cancer in a human subject, comprising:

collecting a biological sample from the subject; then determining the amount of cadmium in said sample; then providing an indication of increased risk for pancreatic cancer based upon the amount of cadmium determined in said sample, with greater levels of cadmium in said sample as compared to a control population, thus indicating a greater risk of pancreatic cancer in said subject.

11. A method according to claim 10, wherein said biological sample is a biological fluid.

12. A method according to claim 11, wherein said biological fluid is urine.

13. A method according to claim 10, wherein said biological sample is a tissue sample.

14. A method according to claim 13, wherein said tissue sample is selected from the group consisting of blood, hair, liver, kidney, and pancreas.

15. The method according to claim 13, wherein said tissue sample is blood.

16. A method according to claim 13, wherein said tissue sample comprises a blood serum sample.

* * * * *